United States Patent [19]

Quinn

[11] Patent Number: 4,580,573
[45] Date of Patent: Apr. 8, 1986

[54] CATHETER INTRODUCER

[75] Inventor: David R. Quinn, Pembroke Pines, Fla.

[73] Assignee: Medical Device Development Corporation, Inc., Lauderhill, Fla.

[21] Appl. No.: 543,859

[22] Filed: Oct. 20, 1983

[51] Int. Cl.[4] .............................................. A61M 25/00
[52] U.S. Cl. ................................... 128/657; 604/169; 604/256; 604/283
[58] Field of Search .................... 128/200.26, 656–658; 604/164, 167, 169, 256, 280, 283, 905

[56] References Cited

U.S. PATENT DOCUMENTS

| | | | |
|---|---|---|---|
| 2,844,351 | 7/1958 | Smith | 604/32 |
| 3,304,934 | 2/1967 | Bautista | 604/236 |
| 4,000,739 | 1/1977 | Stevens | 128/658 |
| 4,202,332 | 5/1980 | Tersteegen et al. | 604/164 |
| 4,287,891 | 9/1981 | Peters | 604/905 |

Primary Examiner—Kyle L. Howell
Assistant Examiner—Ruth S. Smith
Attorney, Agent, or Firm—Melvin K. Silverman

[57] ABSTRACT

There is disclosed herein a catheter introducer having an axially disposed cylindrical elastic segment which covers first and second substantially solid cylindrical elements each defining internal and external diameters, each of said annular elements, as well as the elastic segment, disposed radially symmetrically about a common axis. Also provided are means for rotatably securing said first and second elements relative to said common longitudinal axis for facilitating a reduction in diameter of said elastic segment in order to perform a fluid-tight seal against any elongated element placed along and within said longitudinal axis. A catheter so introduced may be advanced, withdrawn, held, or otherwise manipulated without loss of the fluid or atmospheric seal between the internal diameter of the elastic segment and the object introduced.

3 Claims, 6 Drawing Figures

CATHETER INTRODUCER

BACKGROUND OF THE INVENTION

This invention relates to catheter introducers, sometimes termed cannulas, and particularly introducers used for the positioning and manipulating of intra-vascular catheters known as angiographic catheters.

Angiography is a well known and valuable procedure employed to diagnose vascular and organ disease. It involves the introduction of a hollow tubular catheter into one of the major arteries or veins, such as the femora or brachial artery, and advancing and maneuvering the catheter into smaller or branching vessels which are to be studied. After the catheter is in position, a radio-opaque fluid is injected through the catheter into the vascular system to be studied, and an x-ray picture is taken of the thereby x-ray opaque vascular structure.

There are such techniques for introducing such catheters which include the so-called "cut down" method and various modifications of the so called Seldinger technique. The "cut down" technique involves surgically opening a vein or artery and introducing the angiographic catheter directly through the incision. This method inevitably involves the loss of blood through the incision and may also involve venous ligation and arterial repair. The use of this method renders it particularly difficult to employ the same blood vessel when multiple studies are indicated.

An alternative method of cardiac catheterization comprises a modification of the Seldinger technique in which a subcutaneous sheath is introduced into the lumen of a blood vessel: a hollow needle is inserted through the skin and into the lumen. Thereafter, a guide wire is passed through the needle and advanced up the artery. The needle is then removed, leaving the guide wire in the vessel; a sheath and dilator unit are then advanced over the wire and into the vessel and the dilator is removed along the guide wire. In this technique, any type of catheter can be inserted through the sheath into the vessel. To avoid excessive bleeding, and to insure against the possibility of an air embolism, this technique requires that the physician occlude the orifice of the sheath during catheter changes. Therefore, this procedure suffers from the risk of a blood clot migrating to the heart, lungs or extremities. It has been found that blood loss through the annular space between the sheath and the catheter is difficult to avoid. Both of the above methods have been characterized, especially if multiple studies are indicated, by venous thrombosis, subcutaneous hematomas and considerable discomfort to the patient.

One response to the above problems appears in the U.S. Patent No. 4,000,739 to Stevens, entitled Hemostatis Cannula. This invention involves the use of a certain arrangement of intermeshing disc gaskets in order to hold and/or manipulate the catheter within the sheath during angiographic or other catheterization procedures. The device of Stevens, while representing an improvement over prior art therebefore, is still awkward to use in certain situations and, as well, contains the risk of air embolisms, as was the case in the prior art before Stevens. Other pertinent prior art known to the inventor includes U.S. Pat. No. 2,844,351 to Smith, entitled Fluid Flow Control. This device does not solve the above problems in the prior art.

The present invention is believed to be properly classified in U.S. Class 128, Subclass 214.4; and Class 251, Sub-.

In the known prior art, there has not existed a catheter introducer that can accomodate any sized catheter. Also, those catheter sheaths known in the prior art have not had a good capability of sealing in both longitudinal directions of the cannula. In the prior art, such as Stevens, the atmospheric pressure seal of the sheath introducer against below atmosperic pressures has often not been favorable; therefore, leakage (air asperation) has, on occasion, been a problem.

Finally, during the withdrawal of the catheter, prior art devices have had a tendency to leak. That is, during withdrawal (and, on occasion, during advancement), the cannula often would not totally seal the catheter, i.e., a complete sealing in the prior art could occur only when the catheter was not moving relative to the cannula.

Further, in prior art catheters, the advancement of the catheter could not occur if the valve of the introducer was in a closed position.

It is to all of the above shortcomings in the prior art that the present invention is addressed.

SUMMARY OF THE INVENTION

The present catheter introducer comprises a first substantially solid cylindrical annular element defining an internal diameter and an outer diameter; further included in the present catheter introducer is a second substantially solid cylindrical annular element defining internal and outer diameters. Also furnished are means for rotatably securing said first and second elements relative to each other along a common longitudinal axis passing through the centers of the internal diameters of both of said elements. Disposed in fluid securement between said first and second elements is a cylindrical segment of elastic tubing. Said tubing is radially disposed at or beyond the internal diameters of said two elements such that fluid passing through said internal diameters cannot escape the outer diameters thereof, within the region of said elastic segment. By virtue of the above, a catheter passed through both of said internal diameters may, upon a rotation of said first element relative to said second second element, cause a twisting of said elastic segment into a reduced diameter which is capable of thereby holding in place and atmospherically sealing the catheter which has been placed through said elastic segment.

It is therefore an object to provide a catheter introducer having a variable internal diameter so as to provide for the accommodation of any sized catheter or other related devices having a uniform diameter.

It is a further object to provide a catheter introducer including a valve which will seal against pressures exceeding one atmosphere in either direction regardless of the size of the catheter placed therein.

It is a still further object to provide a catheter introducer having a valve which will seal against pressures exceeding one atmosphere in either direction even in the absence of a catheter placed therewithin.

It is a yet further object to provide a catheter introducer and related valve that will seal against any sized guide wire means with minimal leakage thereabout.

It is a still further object to provide a catheter introducer that will fully seal within approximately one-fourth of a rotation of the cap of the cannula.

It is a yet further object to provide a catheter introducer that will automatically close with no leakage or pressure loss, regardless of the size of the catheter employed when such catheter is withdrawn.

It is a still further object to provide a catheter introducer in which the catheter can be advanced or withdrawn through the valve portion of the introducer when the valve is sealed against the catheter.

It is a yet further object to provide a catheter introducer, the valve of which can be positively purged of air prior to usage.

Other objects, advantages and features of the present invention will become apparent to those skilled in the art from the following Detailed Description of the Invention, the drawings, and appended claims.

DETAILED DESCRIPTION OF PREFERRED EMBODIMENT OF INVENTION

Figure 1:
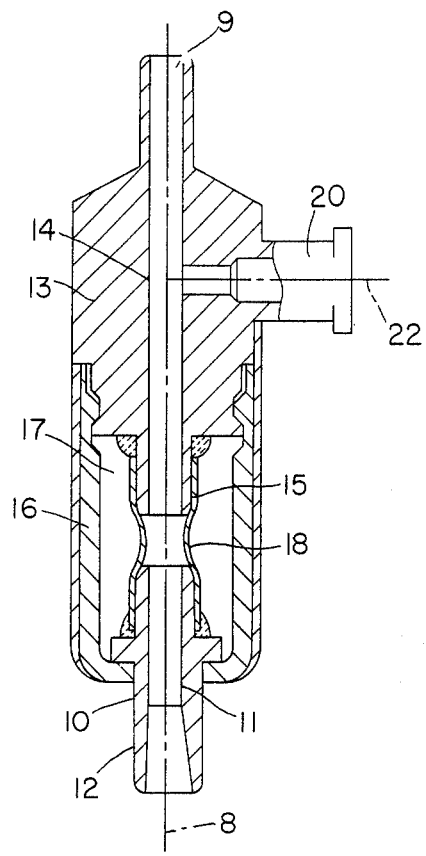
FIG. 1 is a longitudinal cross-sectional view of the inventive catheter introducer.
Figure 2:
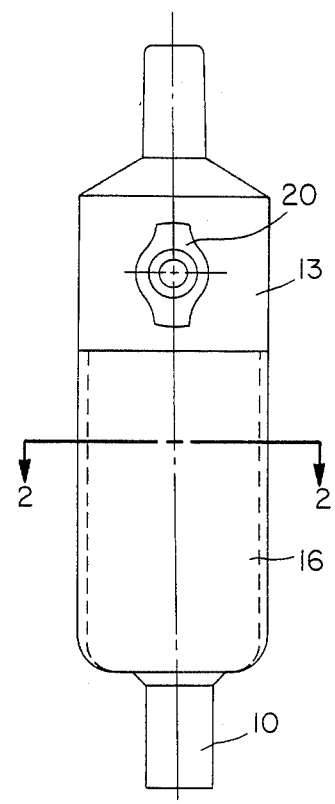
FIG. 2 is a side plan view of the invention.

As seen in FIG. 1, the present inventive catheter introducer comprises a first substantially solid cylindrical annular element 10 defining an internal diameter 11 and an outer diameter 12. The axis of said first solid cylindrical element 10 is defined by a line beginning at a fluid input 8 and ending at a fluid output 9 (line 8-9).

The present catheter introducer further comprises a second element 13 defining, at least in part, a substantially solid cylindrical annular element having an internal diameter 14 and an outer diameter 15. Said second element 13, as in the case of said first element 10, exhibits a longitudinal axis through the internal diameter 14 thereof which coincides with the line 8-9 between the respective inputs and outputs of the present device.

Further provided are means 16 for rotatably securing said first and second elements 10 and 13 respectively, relative to each other, about the common longitudinal axis 8-9 passing through the internal diameters thereof. In the preferred embodiment, rotational securing means 16 is secured to the first element 10 in order to form a "cap" to the device, which rotates relative to the second element 13. However, it is to be appreciated that, in another embodiment, rotatable securing means 16 may be secured to second element 13 such that element 10 is capable of rotation relative to element 16.

With further reference to FIG. 1, area 17 defines a void of rotation which exists between the outer diameters of both said first and second solid annular elements 10 and 13.

Also provided, and of fundamental importance in the operation of the present inventive device, is a cylindrical segment of elastic tubing 18 which is disposed in fluid securement between said first and second elements 10 and 13 respectively.

Said elastic tubing 18 is located radially at or beyond the internal diameters of the elements 10 and 13. The tubing 18, in the preferred embodiment shown in FIG. 1, is placed in fluid tight securement about the outer diameters of the annular elements 10 and 13, the ends of which are positioned toward each other.

By virtue of such fluid tight securement of elastic tubing 18 to annular elements 10 and 13, fluid passing through the internal diameters of said elements 10 and 13 cannot escape outside of the substantially cylindrical volume defined by the internal diameters of elements 10, 13 and 18.

The durometric characteristic of elastic segment 18 is such that it is capable of an elongation of approximately eight fold and, in addition, the ratio of the internal diameter of said elastic segment 18 to the wall thickness thereof falls in the range of 10 to 15.

Shown in FIG. 1 is a secondary port 20 having a longitudinal axis 22.

Figure 3:
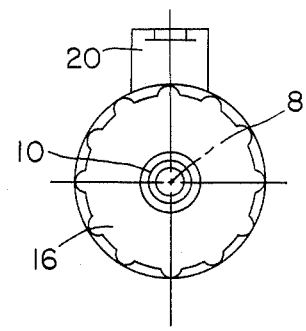
FIG. 3 is a left end view of the catheter introducer.

In FIG. 3 is shown an end view of the device of FIG. 1, showing the general external appearance of the device, in preferred embodiment.

In reference to FIG. 3, a left end view of the device is shown. Therein, a knurled outer surface of rotatable means (cap) 16 is shown. The knurled surface is helpful in the holding and rotating of the catheter intoducer by the user thereof.

It is to be understood that the internal diameters 11 and 14 are to be greater than that of the largest catheter manufactured, thereby assuring that any sized catheter can be used in association with the present device.

In operation, the catheter introducer is used in conjunction with a so called guiding catheter or sheath, which has already been placed in the patient, during prior studies of the patient.

The catheter introducer is attached to the guiding catheter or sheath by use of a lock fitting 23 at the end of the present introducer.

The object 21 to pass through the catheter introducer may be either inserted through the catheter introducer prior to installing the introducer onto the guiding catheter or sheath or may be inserted through the catheter introducer after it has been installed in the patient using the guiding catheter or sheath.

After the catheter introducer has been installed on the guiding catheter or sheath and the object 21 passing through it is in place, the system is purged of air entrapment by first rotating cap 16 to the open position, allowing some liquid to escape. Once some liquid has escaped, purging air from that region, the cap 16 is rotated to the closed position. A syringe filled with saline solution is then attached to the side port tubing 22 and, after withdrawing the air from that annulus, the saline solution is injected into the annulus between the catheter 21 and the passage defined by centerline 8-9, that is, internal diameters 11 and 14.

The physician is then able to turn the cap 16, thereby twisting annular elements 10 and the elastic tubing 18 which is attached thereto. This twisting will typically be a fraction of a rotation and, as a result thereof, the internal diameter of elastic tubing 18 will reduce to a firm, secure fluid-tight engagement against the dilator and/or guide as the same is manipulated or removed by the physician. This mode of operation is shown in FIG. 5 which is an enlarged view of the perspective breakaway view in FIG. 4.

The object or catheter 21 may now be introduced and the guide occupying the axis of line 8-9 thereby passes through first annular element 10, elastic tubing 18, and second annular element 13. Passing along the guide, the catheter 21 will then pass into the lumen of the blood vessel.

Because of the elastic properties of segment 18, any sized catheter or other cylindrical object can be accomodated, with the effective internal diameter of the device being changed by a small fraction of a segment of rotation. Further, the unique design set forth above will seal against pressures exceeding one atmosphere in either direction. This is of considerable importance in that blood loss through the annular space between the catheters and prior art catheter introducers has been difficult to avoid. Also, and of greater improtance, is that the fluid seal of the present device insures against the possibility of an air embolism entering the blood vessel through aspiration.

A diameter of less than 0.001 inch can be held in place through a one-fourth turn of rotation of the cap 16. Thus, the valve can go from a fully open to a fully closed position in approximately one-fourth of a turn. Thereby, the catheter or other elongated object put into the internal diameter of the device, can be advanced or withdrawn through elastic element 18 without loss of the fluid seal against such elongate object.

The present device can be positively purged of air prior to usage.

Figure 4:
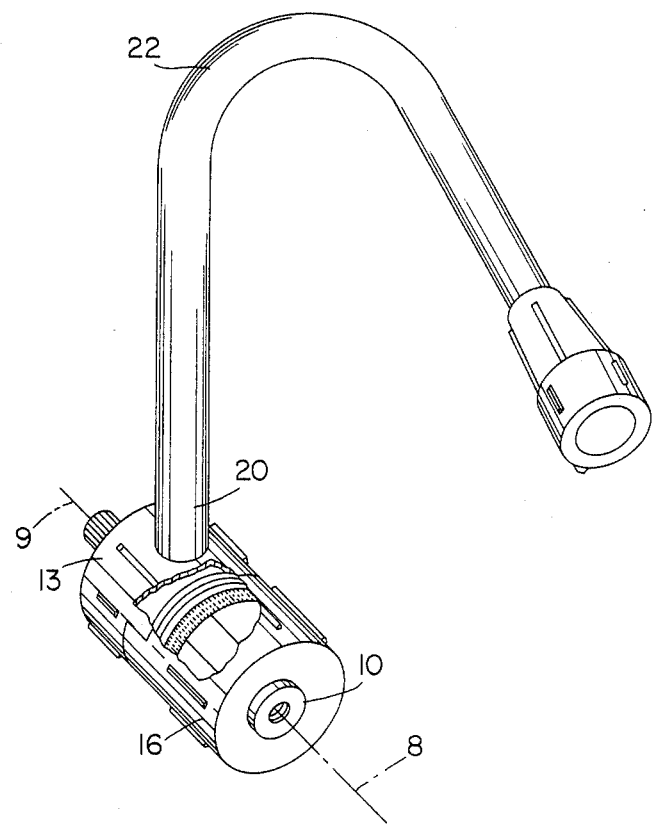
FIG. 4 is an exploded, partially cut-away view of a preferred embodiment of the invention.
Figure 6:
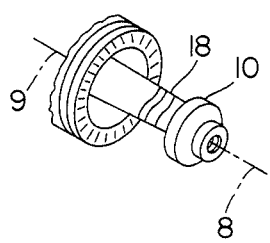
FIG. 6 is an enlarged perspective view of the flexible tubing element in a closed mode with no object passing through the flexible tubing element.
Figure 5:
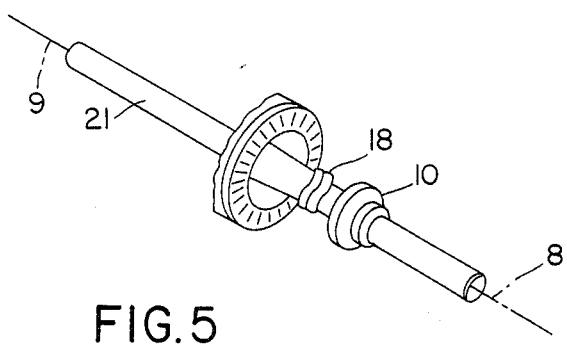
FIG. 5 is an enlarged perspective view of the flexible tubing element of the catheter introducer in a closed mode, holding a catheter.

It is noted in FIGS. 1, 3 and 4 that the device can be provided with a side port 20 having a fluid communication with the internal diameter 14 of the second annular element 13. This feature affords the possibility of introducing a second medical fluid into the internal diameter 14 and, thereby, introducing such fluid into the annular volume existing between the internal diameter 14 and the outside diameter of catheter 21. This feature is important where it is necessary to provide a constant supply of a secondary substance, such as hepernine saline solution into the body.

In operation, the present catheter introducer has been found to be superior to the so called tricuspid valve and the so called Towhy-Borst Valve, one form of which is embodied in above referenced U.S. Pat. No. 4,000,739.

It is thus seen that through the use of an axially disposed cylindrically elastic sleeve, there is provided a means for holding and manipulating annular cylindrical objects such as catheters which will seal off the possible flow of blood in the outer direction and will prevent air aspiration in the opposite direction.

In typical usages, once a catheter has been maneuvered into position, a radio-opaque fluid is injected therethrough, and an x-ray photograph may be taken of the then radio-opaque vascular system of the organ being studied.

If multiple studies are indicated, or if the catheter has not been correctly positioned, it is a simple matter to remove the catheter and to introduce another, even utilizing the same guide wire and/or dilator in this process.

It is to be appreciated that, while there has been herein described a preferred embodiment of the invention, the invention may be embodied in other forms without departing from the spirit or principles as set forth herein, and within the scope of the appended claims, and changes within the meaning, range, and equivelency of the invention and appended claims are encompassed herein.

Having thus described my invention what I claim as new, useful, and non-obvious, and accordingly, secure by Letters of Patent of the United States is:

1. A catheter introducer, comprising:
    (a) a first annular element comprising a substantially solid cylindrical element defining an internal diameter and an outer diameter;
    (b) a second annular element comprising a substantially solid cylindrical element defining an internal diameter and an outer diameter;
    (c) means for rotatably securing said first and second elements relative to each other and about a common longitudinal axis passing through the centers of the internal diameters of both of said annular elements; and
    (d) a cylindrical segment of elastic tubing, said tubing having elongation properties of at least 800% and having a ratio of internal diameter to wall thickness in the range of 10:1 to 15:1, said segment disposed in a fluid-tight securement, between said first and second annular elements, radially at or beyond the internal diameters of said annular elements, wherein a catheter-like object passing through both of said internal diameters may, upon a fractional rotation of said first element relative to said second element, cause a resultant spiral wrap-around of said object by said elastic segment and therein a reduced diameter of the elastic segment, such wrap-around and reduced diameter thereby causing both intimate contact with said catheter-like object and a continuous, integral seal about said object,
    whereby said object will be held in place by said continuous, integral seal of said elastic segment, thereby keeping the surface of the catheter-like object, relative to the catheter introducer, sealed in both directions relative to atmospheric and body fluid pressures, this permitting, if desired, axial movement and rotation of said catheter-like object within said elastic segment without loss of said continuous integral seal.

2. The catheter introducer recited in claim 1 in which said elastic segment is secured to and about the outside diameters of said annular elements in the region where said elements face each other.

3. The catheter introducer recited in claim 1 in which said second annular element includes a side port having fluid communication with the internal diameter of said second element,
    whereby a medical fluid may be injected through said side port and into the annular volume existing between the internal diameter of said second element and the outer diameter of said catheter-like object.

* * * * *